United States Patent [19]

Fagan, Jr. et al.

[11] 4,179,809
[45] Dec. 25, 1979

[54] DENTAL IMPLANT

[76] Inventors: Maurice J. Fagan, Jr.; Maurice J. Fagan, III, both of 5360 Peachtree-Dunwoody Rd., NE., Atlanta, Ga. 30342

[21] Appl. No.: 804,383

[22] Filed: Jun. 7, 1977

Related U.S. Application Data

[63] Continuation-in-part of Ser. No. 581,419, May 27, 1975, Pat. No. 4,050,157.

[51] Int. Cl.² ............................................. A61C 8/00
[52] U.S. Cl. ................................................. 433/176
[58] Field of Search .................... 32/10 A; 128/92 C

[56] References Cited

U.S. PATENT DOCUMENTS

| | | | |
|---|---|---|---|
| 3,738,004 | 6/1973 | Edelman | 32/10 A |
| 3,798,771 | 3/1974 | Edelman | 32/10 A |
| 3,849,888 | 11/1974 | Linkow | 32/10 A |
| 3,928,914 | 12/1975 | Kozlovsky | 32/10 A |
| 4,050,157 | 9/1977 | Fagan, Jr. et al. | 32/10 A |

FOREIGN PATENT DOCUMENTS

| | | | |
|---|---|---|---|
| 2237598 | 2/1974 | Fed. Rep. of Germany | 32/10 A |
| 1305478 | 1/1973 | United Kingdom | 32/10 A |

*Primary Examiner*—Russell R. Kinsey
*Assistant Examiner*—John J. Wilson
*Attorney, Agent, or Firm*—Clarence A. O'Brien; Harvey B. Jacobson

[57] ABSTRACT

A dental implant for anchoring attachments to the jawbone including an endosseous blade-like base embedded entirely within the bone tissue of the mandibular or maxillary ridge. A juxtaosseous support abutment is connected to the base by a shank having a neck portion spaced from the base and confined to the gingival. The base is received within a trough surgically cut into the jawbone and stabilized therein by cross-sectionally rounded enlargements of edge portions extending in mesial-distal directions relative to the shank.

6 Claims, 25 Drawing Figures

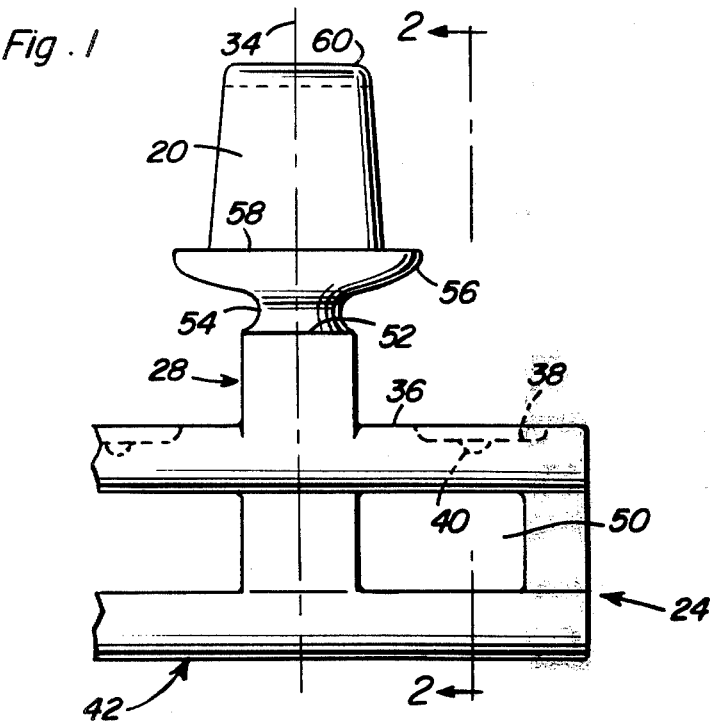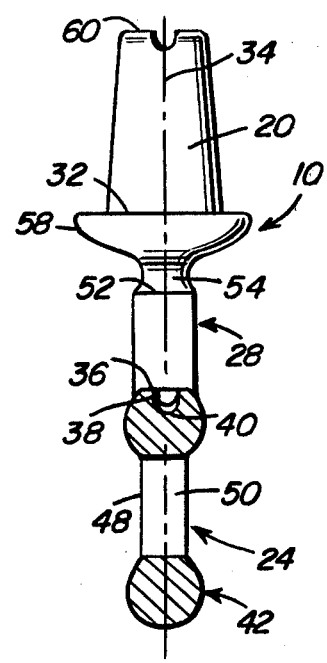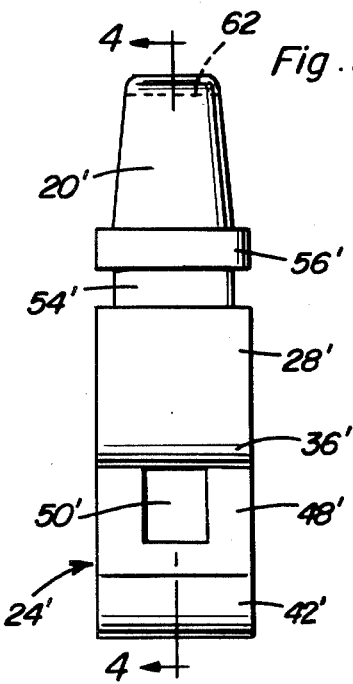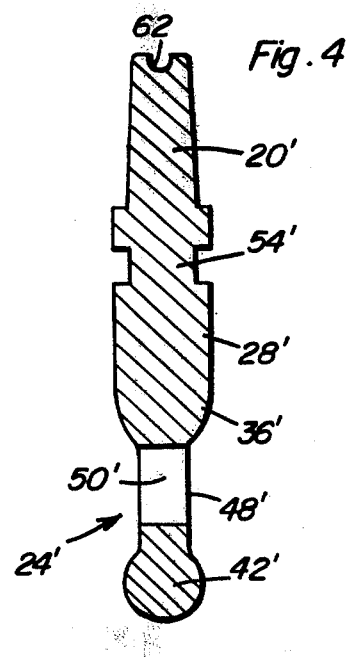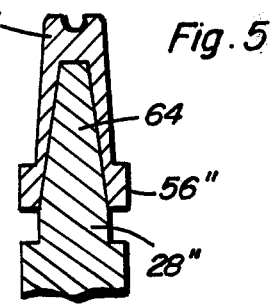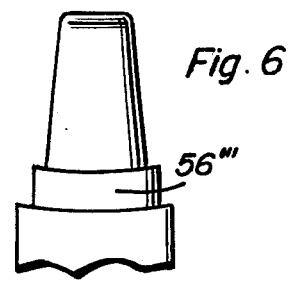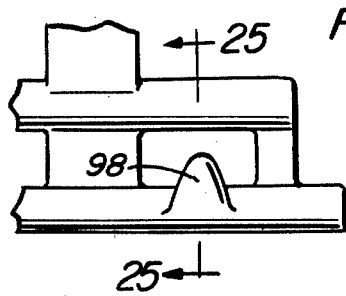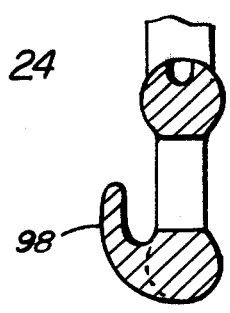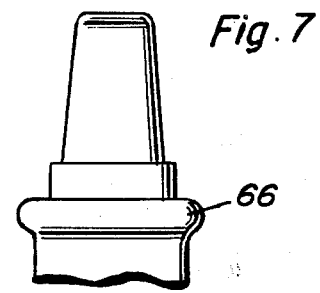

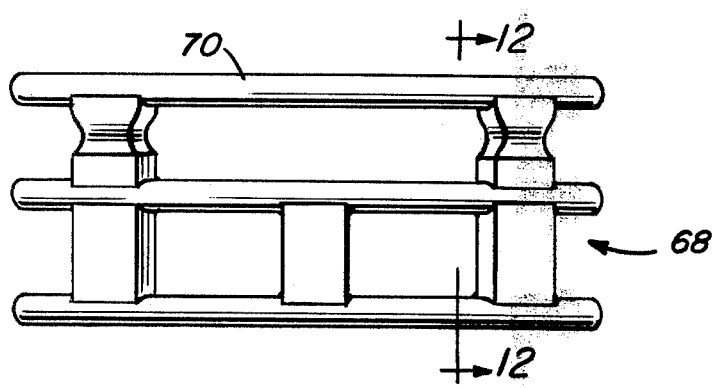
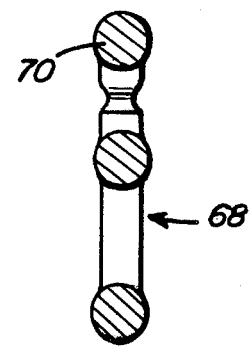
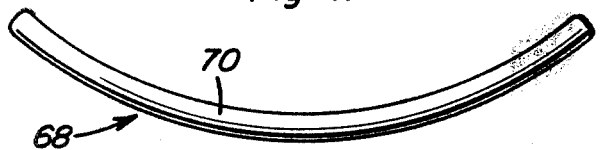
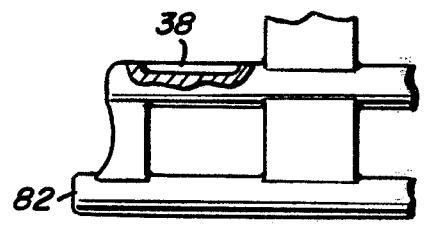
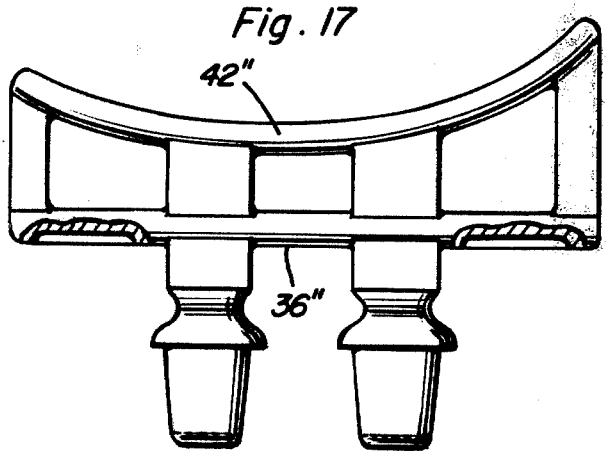
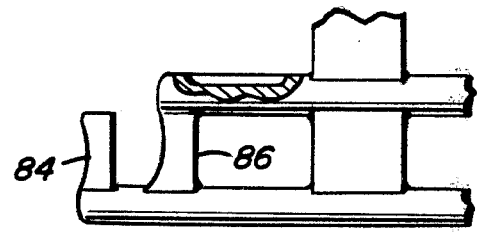
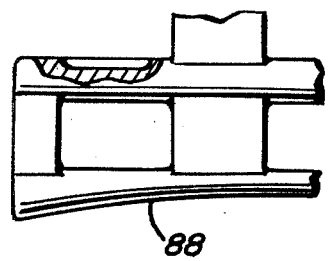
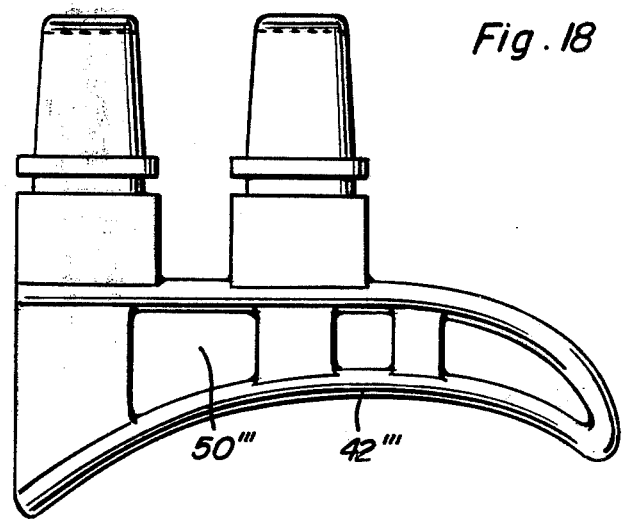

DENTAL IMPLANT

CROSS-REFERENCE TO RELATED APPLICATION

This is a continuation-in-part of our co-pending application Ser. No. 581,419, filed May 27, 1975, for Dental Implant, now U.S. Pat. No. 4,050,157.

BACKGROUND OF THE INVENTION

1. Field of the Invention

This invention relates to the permanent anchoring of dental attachments to the jawbone of a patient by use of a metallic implant.

The use of implants in the bone tissue of a patient for anchoring of dental attachments such as artificial teeth and crowns are well known. In some prior art arrangements, the implant base is of an elastically resilient type occupying the socket from which the root portion of a natural tooth was extracted. Other prior art implants feature a relatively thin rigid blade embedded in the bone tissue without regard to any socket remaining after extraction of the natural tooth. The blade-type implant heretofore proposed is provided with a sharp edge at its free end capable of being directly forced or driven into the bone structure in order to embed and retain the implant in place. A major problem arising with such dental implants resides in the unfavorable reaction of bone tissue to forces transmitted through the dental implant. Occlusal forces applied either obliquely or producing a horizontal component when acting upon cuspal inclinations, cause mobility and/or injury because of the ill effects of the leverage associated with such dental implants. Very often, such prior dental implants will loosen or cause periodontal destruction to a greater extent than that occasioned with natural teeth in a weakened environment.

It is, therefore, an important object of the present invention to provide a dental implant for anchoring dental attachments in such a manner as to improve reaction of bone tissue to transmitted forces by a beneficial modification in the leverage arrangement of the dental implant as compared to that of the tooth and the leverage arrangements associated with prior dental implants.

2. Description of the Prior Art

Applicants are presently aware of the following patents, copies of which are submitted herewith:
U.S. Pat. Nos:
  2,721,387—Oct. 25, 1955—Ashuckian
  3,465,441—Sep. 9, 1969—Linkow
  3,729,825—May 1, 1973—Linkow et al.
  3,798,771—Mar. 26, 1974—Edelman
  3,829,972—Aug. 20, 1974—Pasqualini et al.
  3,849,888—Nov. 26, 1974—Linkow
  3,977,081—Aug. 31, 1976—Zambelli et al.
British Pat. Nos:
  1,278,966—June 21, 1972—Edelman 1,278,997—June 21, 1972—Edelman
German Pat. No.
  2,522,433—May 21, 1975—Pasqualini et al.

The foregoing patents disclosed the prior art heretofore alluded to.

SUMMARY OF THE INVENTION

In accordance with the present invention, a dental implant is arranged to stabilize itself once embedded within the bone tissue in order to better resist those occlusal forces tending to rotate the tooth about its center of rotation causing periodontal destruction and loosening of the implant. This is effected by a special design of the implant body which balances moments tending to produce implant rotation. As in the case of the prior art aforementioned, the implant body of the present invention includes a substantially thin endosseous blade-like base embedded within the bone tissue of the jawbone. Unlike the prior art implant bodies of the blade type, however, the base of the dental implant according to the present invention is provided with a rounded bottom edge in order to produce a stabilizing effect on the implant base by preventing buccal-lingual movement. The other edge of the implant base is spaced from the crest of the ridge by a distance equal to a rectangular shoulder portion of a shank projecting from this edge of the base toward a juxtaosseous support abutment exposed above the gum line and on which an attachment is secured. The shank projecting from the base is provided with a necked down portion confined to the gingival and terminating in an enlarged gingival collar from which the support abutment projects. A peripheral shoulder surface on the gingival collar is exposed in surrounding relation to the support abutment in order to receive the attachment such as the connecting crown of a fixed bridge. The necked down portion of the shank provides a tight gingival attachment. The base extends laterally in a mesial-distal direction from the shank with the side surfaces thereof recessed and provided with at least one substantially rectangular opening through which bone tissue may grow after the implant body has been inserted into a trough surgically cut into the jawbone. The edge portion of the implant base from which the shank projects is provided with an edge surface within which a groove and notch is formed for an implant inserting instrument or tool.

The continous bottom edge on the implant base and the recessed intermediate portions of the base along its length in the mesial-distal direction, prevent loosening of the implant once properly inserted with the proper prosthetic appliance thereon. The foregoing arrangement is such that occlusal forces applied to the dental attachment will result in an equilibrium of moments and a favorable transmission of tensile forces so that the bone is stimulated and deposited through the rectangular openings in the implant base by the adjacent trabeculated bone. The implant body is thus retained in place with a minimum of fibrous connective tissue separating the metal portion of the implant base from the trabeculated bone.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWING FIGURES

FIG. 1 is a partial front elevation view of one form of dental implant.

FIG. 2 is a side section view taken substantially through a plane indicated by section line 2—2 in FIG. 1.

FIG. 3 is a front elevation view of another form of dental implant.

FIG. 4 is a side section view taken substantially through a plane indicated by section line 4—4 in FIG. 3.

FIGS. 5, 6 and 7 are partial views illustrating modifications of the implant shown in FIGS. 3 and 4.

FIGS. 10 and 11 are front and top views of another form of dental implant.

FIG. 12 is a section view taken substantially through a plane indicated by section line 12—12 in FIG. 10.

FIGS. 14, 15 and 16 are partial front elevation views of an implant showing certain modifications of the base portion shown in FIG. 1.

FIGS. 17 and 18 are front elevation views showing additional forms of dental implants.

FIG. 24 is a partial front elevation view showing yet another modification of the base portion of the implant shown in FIG. 1.

FIG. 25 is a partial section view taken substantially through a plane indicated by section line 25—25 in FIG. 24.

DETAILED DESCRIPTION OF PREFERRED EMBODIMENTS

Figure 13:
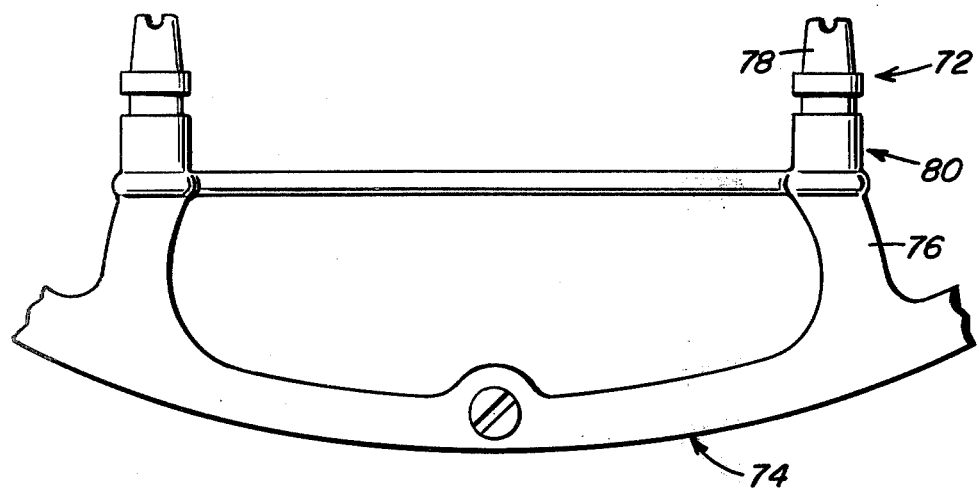
FIG. 13 is a side view of yet another type of dental implant.

Referring now to the drawings in detail, FIGS. 1 and 2 illustrate one form of implant body generally referred to by reference numeral 10 adapted to be embedded in the lower mandible of a patient as described in our prior copending application, aforementioned. The implant body 10 includes a rigid blade-like base generally referred to by reference numeral 24. The base is embedded entirely within the bone tissue spaced from the ridge crest. An abutment support 20 is connected to the base by means of a shank more massive than the base and generally referred to by reference numeral 28. The shank 28 thus projects from the base 24 to the ridge crest and extends through the gingival to the gum line at which the shank is connected to the abutment support 20. A root axis 34 extends centrally through the abutment support 20 and the shank 28 to which it is connected.

The base 24 extends transversely of the root axis from the shank in a mesial-distal direction when implanted within the bone tissue. The longitudinal edge portion 36 of the base from which the shank 28 extends, is formed with a flat edge surface adapted to be spaced from the ridge crest by a predetermined distance such as 2.5 millimeters. An elongated groove 38 is formed in the edge 36 for receiving an inserting instrument. A circular notch 40 is also formed in the edge surface 36 for receiving the inserting instrument. The edge 36 as well as the other longitudinal edge portion 42 of the base are cross-sectionally rounded as shown in FIG. 2. The two edge portions 36 and 42 of the base extend substantially beyond the shank 28 in the embodiment shown in FIG. 1. The side surfaces 48 of the base intermediate the spaced edge portions 36 and 42, are inwardly recessed and are formed with spaced, substantially rectangular openings 50 offset from the shank 28 through which bone tissue is adapted to grow for anchoring of the implant body therein.

The shank 28, as shown in FIGS. 1 and 2, includes a cross-sectionally rectangular shoulder portion 52. The shoulder portion extends from the base to the ridge crest and, therefore, determines the depth to which the base is embedded within the bone tissue from ridge crest. Extending from the shoulder portion 52 is a neck portion 54. The neck portion 54 is cross-sectionally smaller than the shoulder portion 52 or the abutment support 20 to which it is connected and flares radially outwardly into a gradually enlarged gingival collar 56 having a peripheral shoulder surface 58 adapted to be exposed at the gum line in surrounding relation to the abutment support 20. The shoulder surface 58 which may be 0.8 millimeters wide, for example, forms an abutment surface for a connecting crown. The neck portion 54 between the shoulder portion 52 and the gingival collar forms a tight fit within the gum tissue to which it is confined.

The abutment support 20 is of a non-planar shape as compared to the base 24 and tapers from the radially enlarged gingival collar 56 in a converging direction to a top surface 60. The sides of the abutment support are rounded.

In FIGS. 3 and 4, a single tooth implant 10' is shown having the same basic structural features as implant 10, including an implanted base portion 24' having spaced edge portions 36' and 42' that are cross-sectionally rounded and a recessed side portion 48' that is provided with a rectangular opening 50'. A massive shank 28' extends from the edge portion 36' and is connected by a neck 54' to a gingival collar 56' to which the support 20' is connected. An inserting groove 62 is formed on the top of support 20'.

FIG. 5 shows a modification wherein the support 20" is separately formed integral with the gingival collar 56" and is wedged onto a conical formation 64 projecting from the neck 28". In FIG. 6, the gingival collar 56''' is arcuate in shape at the shoulder surface from which the support abutment extends. In FIG. 7, the shank is enlarged at 66. The foregoing shank-neck designs may be utilized interchangeably with different base portion designs.

An anterior endosseous implant 68 is shown in FIGS. 10, 11 and 12. In this form of implant, the base portion is arcuate in shape and includes an arcuate connecting bar 70 between the support abutments. The bar 70 is also rounded in cross section as more clearly seen in FIG. 12.

FIG. 13 is a lateral view of a subperiosteal implant 72, wherein the structure 74 interconnects the base portions 76 adapted to anchor a pair of abutment supports 78. The base portions 76 and shank structure 80 projecting therefrom are similar to the arrangement described with respect to FIGS. 3 and 4.

In FIG. 14, a base portion of an implant as described with respect to FIGS. 1 and 2, is modified by extension of the free edge portion to an end 82 spaced beyond the other edge portion in which the tool insertion groove 38 is located. In FIG. 15, a further modification is shown in the form of a projection 84 on the extended lower edge portion, spaced from the end 86 of the base for additional anchoring purposes. The width of the lower edge portion is varied to present a curved surface 88 for the lower edge portion in FIG. 16.

An implant body for the upper or maxillary jaw is shown in FIG. 17 which is basically similar to the implant body 10 shown in FIG. 1. Two shanks and abutment supports project from the base in FIG. 17, but the rounded edge portion 42" associated with the base in FIG. 17 is not parallel to the straight edge portion 36" as in the other embodiments but extends along a curvature determined by the portion of the maxillae within which the dental implant is embedded.

In FIG. 18, yet another embodiment of a dental implant for the maxillae is shown wherein a pair of shanks and abutment supports project non-symmetrically from a base which is provided with abutment supports and associated opening 50′′′ between the two shanks. Also, the rounded edge 42′′′ associated with the base in FIG. 18, is provided with an arcuate curvature.

Figure 19:
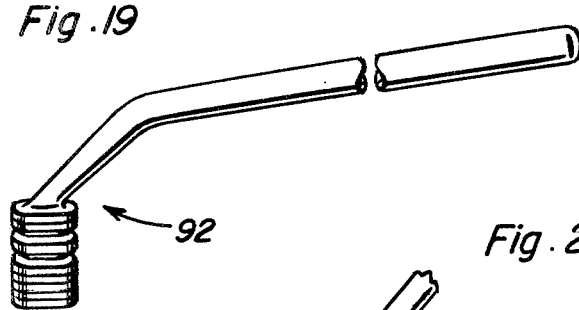
FIGS. 19, 20, 21, 22 and 23 illustrate different instruments or tools for handling the dental implants.
Figure 20:
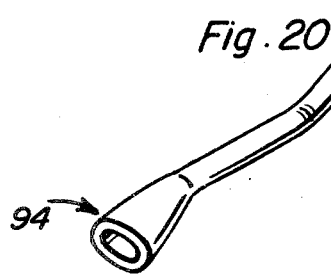
Figure 21:
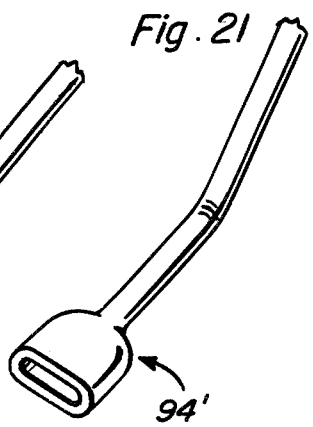
Figure 22:
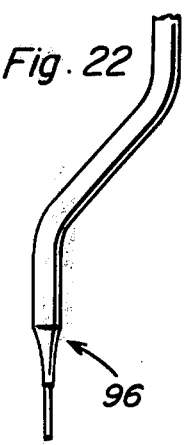
Figure 23:
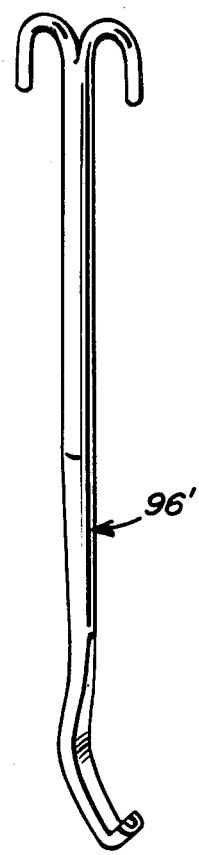
Figure 8:
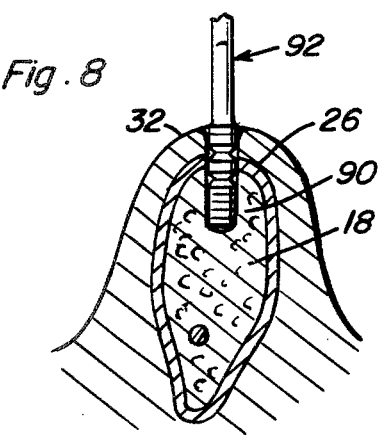
FIGS. 8 and 9 are transverse section views through a typical lower jawbone showing the implant procedure associated with the present invention.
Figure 9:
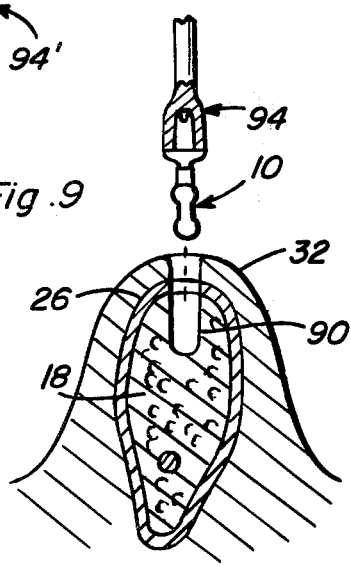

The various dental implants hereinbefore described are designed for different mandible and maxillae locations and for different types of permanent tooth restorations. Once the type of restoration and location of the dental implant is decided upon, the selected dental implant is embedded in the mandible or maxillae in accordance with approved procedures. Briefly, the implant insertion procedure includes making of a clean incision through the gingival tissue 32 and periosteum in the bony crest 26 as shown in FIGS. 8 and 9. The gingival and periosteum is then retracted after which a recession or trough 90 of the proper width and depth is made in the bone 18 in order to accommodate the implant base and stabilizer. An instrument 92 is used to measure the depth. The implant body which has been sterilized is then inserted into the prepared trough with an instrument 94 as shown in FIG. 9 and firmly seated by an instrument 96 received in groove 38 or notch 40. The shoulder portion 52 of the shank will guide the surgeon in finally positioning the implant body with the edge 36 of the base spaced 2.5 millimeters from the bony crest. When properly positioned, the abutment support 20 will be properly aligned parallel to the natural abutment teeth in order to insure proper inserting of a final bridge, for example. The tissues are then sutured in place about the protruding abutment support 20. After the sutures are removed a permanent crown may be placed over the support and cemented in place. FIGS. 19, 20 and 22, respectively, show the depth measuring, implant positioning, and implant seating instruments 92, 94 and 96. FIG. 21 shows an instrument 94′ adapted to engage two closely spaced abutment supports of an implant of such a type. In FIG. 23, an implant retracting instrument 97 is shown.

FIGS. 24 and 25 illustrate yet another modification of the implant shown in FIGS. 1 and 2. In this embodiment, the lower edge portion of the base portion is provided with a rigid lateral stabilizer element 98. The element 98 extends upwardly in laterally spaced relation to the base overlying the opening therein.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A dental implant for anchoring an attachment to a jawbone, comprising an endosseous blade type of base having two spaced edge portions, a shank projecting from one of the edge portions on which the attachment is supported, said edge portions being elongated relative to the shank in a mesial-distal direction and endosseous stabilizer means adapted to be embedded with the base entirely within said jawbone, including a rounded cross-sectional enlargement of the base continuously along the other of the spaced edge portions.

2. The combination of claim 1 wherein said one of the edge portions is provided with a tool receiving groove, whereby the other of the edge portions of the implant base may be seated within a trough precut into the jawbone.

3. A device for permanently anchoring an attachment in the mouth of a patient, said device comprising an implanting portion in the form of a comparatively thin blade having an opening provided therein and a support portion adapted to have a juxtaosseous structure secured thereon, said implanting portion including a first edge from which the support portion extends, the first edge having a tool receiving groove spaced from the support portion through which the implanting portion is seated within a trough cut into the bone structure of the patient, and a second edge spaced from the first edge remote from the support portion, said second edge being formed entirely as a cross-sectionally rounded enlargement of the blade extending in a mesial-distal direction relative to the support portion to stabilize the implanting portion within the bone structure.

4. The combination of claim 3 including a rigid stabilizer element extending laterally from the second edge in overlaying relation to said opening.

5. A dental implant for anchoring an attachment, comprising a blade having at least one opening formed therein, a shank projecting from the blade in offset relation to the opening, and a support connected to the shank to which the attachment is adapted to be secured, said blade including recessed side surfaces through which the opening extends, a first edge from which the shank projects and a second elongated edge remote from the shank that is a cross-sectionally rounded enlargement of the blade.

6. A bone implant having a thin blade portion adapted to be implanted in a jawbone and at least one integral neck portion projecting from said blade portion externally of the bone, said blade portion having at least one longitudinal end remote from said neck portion, two elongated edges extending in spaced relation to each other from said end transversely of the neck portion and a tool-receiving recess formed in one of said edges between the neck portion and said end, the other of the edges being formed by a continuous cross-sectionally rounded enlargement of the blade portion to produce a stabilizing effect.

* * * * *